(12) United States Patent
Patel et al.

(10) Patent No.: US 11,679,139 B2
(45) Date of Patent: Jun. 20, 2023

(54) COOLING SPRAY

(71) Applicant: GLAXOSMITHKLINE CONSUMER HEALTHCARE HOLDINGS (US) LLC, Wilmington, DE (US)

(72) Inventors: Shivangi Akash Patel, Mechanicsville, VA (US); Renee Nelson, Brandon, FL (US)

(73) Assignee: GLAXOSMITHKLINE CONSUMER HEALTHCARE HOLDINGS (US) LLC, Wilmington, DE (US)

( * ) Notice: Subject to any disclaimer, the term of this patent is extended or adjusted under 35 U.S.C. 154(b) by 28 days.

(21) Appl. No.: 17/218,628

(22) Filed: Mar. 31, 2021

(65) Prior Publication Data

US 2022/0313763 A1 Oct. 6, 2022

(51) Int. Cl.
| | | |
|---|---|---|
| *A61K 36/185* | (2006.01) | |
| *A61K 9/00* | (2006.01) | |
| *A61K 9/12* | (2006.01) | |
| *A61K 47/36* | (2006.01) | |
| *A61K 47/10* | (2017.01) | |

(52) U.S. Cl.
CPC .......... *A61K 36/185* (2013.01); *A61K 9/0014* (2013.01); *A61K 9/124* (2013.01); *A61K 47/10* (2013.01); *A61K 47/36* (2013.01)

(58) Field of Classification Search
CPC ....... A61K 47/10; A61K 47/36; A61K 9/0014
See application file for complete search history.

(56) References Cited

U.S. PATENT DOCUMENTS

| | | | |
|---|---|---|---|
| 2009/0068128 A1* | 3/2009 | Waddington | ......... A61K 8/9789 424/59 |
| 2015/0118165 A1* | 4/2015 | Rudolph | ............... C07C 69/608 560/126 |

OTHER PUBLICATIONS

Walgreens Soothing Hemorrhoid Spray with Lidocaine https://www.walgreens.com/store/c/walgreens-soothing-hemorrhoid-spray-with-lidocaine/ID=prod6385501-product. Retrieved Mar. 26, 2021.
Blairex Hem-Spray https://www.amazon.com/Hemspray-BLAIREX-HEMSPRAY/dp/B000V7TQB6. Retrieved Mar. 26, 2021.
Walgreens Soothing Hemorrhoid Spray with Lidocaine. https://www.walgreens.com/store/c/walgreens-soothing-hemorrhoid-spray-with-lidocaine/ID=prod6385501-product.
Thayers Alcohol-Free Witch Hazel Facial Mist Toner https://www.walgreens.com/store/c/thayers-alcohol-free-unscented-witch-hazel-facial-mist-toner-unscented,-unscented/ID=30039.
T.N. Dickinson's Witch Hazel Astringent Spray https://www.amazon.com/Dickinsons-Natural-Astringent-Spray-Ounce/dp/B07DD4QD8Y?language=en_US.

* cited by examiner

*Primary Examiner* — Mark V Stevens
(74) *Attorney, Agent, or Firm* — Christopher S. Dodson

(57) ABSTRACT

A liquid composition comprising witch hazel; glycerin; dehydrated xanthan gum; and water.

17 Claims, 3 Drawing Sheets

COOLING SPRAY

TECHNICAL FIELD

The invention is generally related to pharmaceutical compositions, and, more specifically, to sprayable liquid pharmaceutical compositions.

BACKGROUND

Hemorrhoids are a common anorectal condition where veins in the anus and lower rectum become swollen. It is estimated that nearly 3 out of four adults will have hemorrhoids at some point in their life. There are two main types of hemorrhoids—internal and external. Internal hemorrhoids are usually painless unless they become thrombosed or necrotic and are often only discovered when rectal bleeding occurs during or following a bowel movement. External hemorrhoids are different from internal hemorrhoids in that they are often very painful if touched, and are commonly accompanied by itching or irritation, swelling, and bleeding in the anorectal region.

There are many commercial products available to alleviate the pain and discomfort of hemorrhoids, especially external hemorrhoids. These include wipes, topical creams, and topical gels containing cooling or numbing agents such as lidocaine, camphor, witch hazel, and the like. While these ingredients can be effective at providing relief, current commercial products are not necessarily ideal. For example, medicated wipes can be difficult to dispose after use. Additionally, wipes, creams, and gels require one to physically touch the sensitive area, causing pain during application of the product, and, given that this is typically the anorectal area, application can be unsanitary. Creams and gels also present the problem of being messy due to the need to apply the product using one's fingers and hands.

Spray delivery of cooling or numbing agents alleviates some of the disadvantages of wipes, creams, and gels by offering an indirect contact application route and sanitary "touchless" features. However, few of such formulations are available to consumers and those that are available rate very low in consumer satisfaction for a variety of reasons. For example, an ideal spray product will have a narrow spray target, apply a fine mist that forms an even coat that dries quickly, spray upside down, and will readily cling to skin without dripping and running. Unfortunately, currently marketed spray formulations all suffer from deficits in one or more of these factors, with the most common being a propensity to drip or run down the skin of a user after application.

Accordingly, there is a need for improved spray formulations that achieve or alleviate one or more of the deficiencies found in conventional spray formulations.

SUMMARY

In one aspect, a liquid composition comprises witch hazel; glycerin; dehydrated xanthan gum; and water. In some cases, the dehydrated xanthan gum is present in the composition in an amount of 0.05 to 3 wt. %. In some instances, the dehydrated xanthan gum is present in the composition in an amount of 0.05 to 1.0 wt. %. In some cases, the dehydrated xanthan gum is present in the composition up to 0.5 wt. %. In some embodiments, the liquid composition comprises 0.1-0.5 wt. % dehydrated xanthan gum.

In some embodiments, the liquid composition comprises 10-50 wt. % witch hazel. In some cases, the liquid composition comprises 10-45 wt. % glycerin.

The liquid composition further comprises water in some embodiments. In some instances, the liquid composition comprises 30-70 wt. % water.

In one embodiment, a liquid composition described herein comprises 10-50 wt. % witch hazel; 10-45 wt. % glycerin; 0.05 to 1 wt. % dehydrated xanthan gum; and water. This liquid composition can further comprise a propellant in some cases.

In some instances, liquid compositions described herein further comprise one or more of a chelating agent, an emollient, a humectant, a preservative, a pH modifier, and a propellant. The chelating agent can comprise disodium EDTA, edetic acid, or a combination of both. The emollient can comprise one or more of *Aloe barbadensis* leaf juice, shea butter, vitamin E or pharmaceutically acceptable salts thereof, or any combination thereof in some cases. The humectant can comprise one or more of propylene glycol, sorbitol, glycerin, or any combination thereof in some embodiments. The preservative comprises one or more of sodium benzoate, benzyl alcohol, methyl paraben, propyl paraben, or any combination thereof in some instances. In some embodiments, the pH modifier comprises one or more of sodium citrate, citric acid, acetic acid, maleic acid, tartaric acid, sodium acetate, sodium hydroxide, potassium hydroxide, or any combination thereof. In some cases, the propellant comprises one or more of isobutane, propane, N-butane, or any combination thereof.

In another aspect, a method of treating pain or inflammation in a mammalian (e.g., human or animal) subject comprising topically administering a therapeutically effective amount of a liquid composition described herein to a mammalian subject in need thereof.

DETAILED DESCRIPTION

Figure 1:
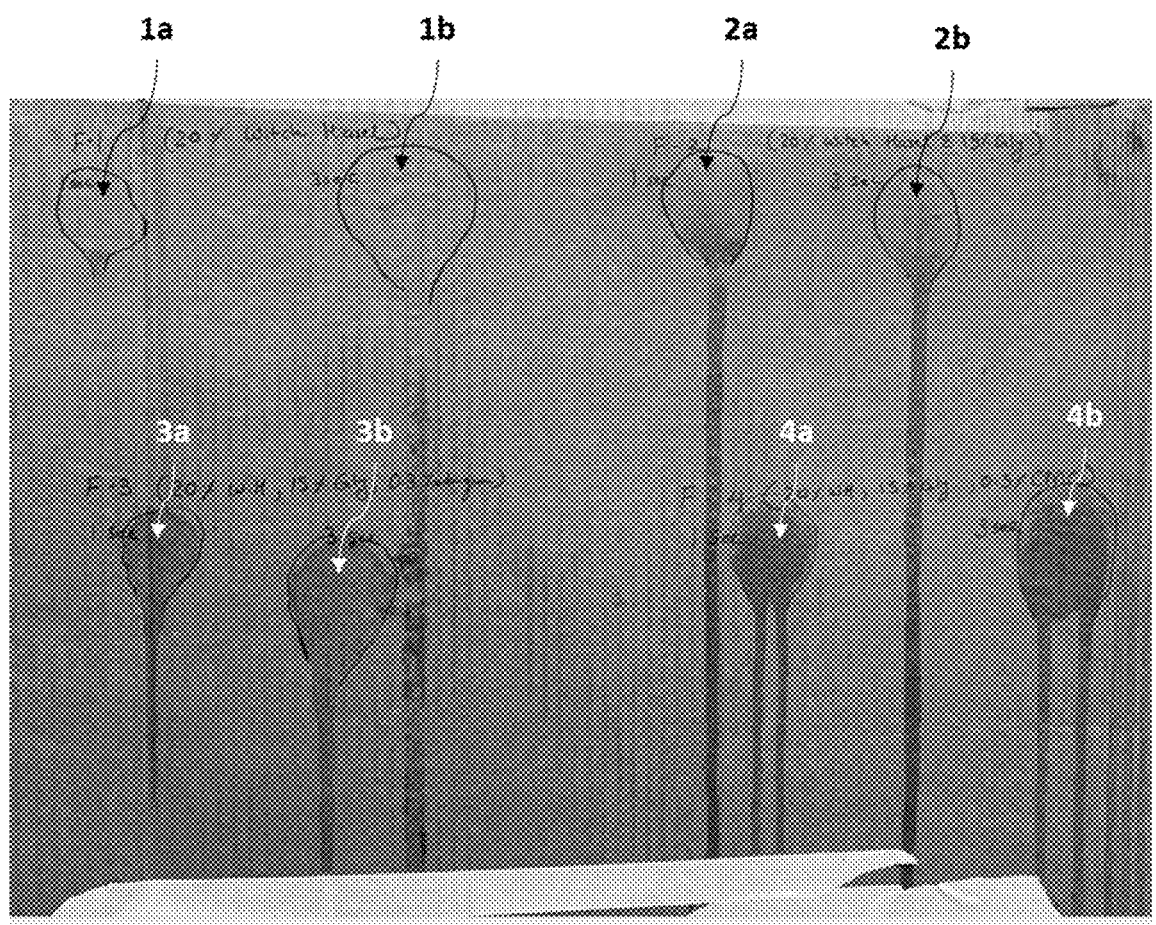
FIG. 1 is a photographic image comparing the physical properties of Formulations 1-4 described herein having conventional thickening agents.

Embodiments described herein can be understood more readily by reference to the following detailed description, examples, and figures. Elements, apparatus, and methods described herein, however, are not limited to the specific embodiments presented in the detailed description, examples, and figures. It should be recognized that the exemplary embodiments herein are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" or "5 to 10" or "5-10" should generally be considered to include the end points 5 and 10.

It is further to be understood that the feature or features of one embodiment may generally be applied to other embodiments, even though not specifically described or illustrated in such other embodiments, unless expressly prohibited by this disclosure or the nature of the relevant embodiments. Likewise, compositions and methods described herein can include any combination of features and/or steps described herein not inconsistent with the objectives of the present disclosure. Numerous modifications and/or adaptations of the compositions and methods described herein will be readily apparent to those skilled in the art without departing from the present subject matter.

A liquid composition suitable as a spray product is described herein. The composition, when applied to a human or mammalian skin as a spray, can in some embodiments achieve or alleviate one or more of the deficiencies found in conventional spray formulations. For example, the composition can have a narrow spray target, be applied as a fine mist that forms an even coat that dries quickly, be sprayed upside down, and can readily cling to skin without dripping and running. The described compositions can be used to provide relief to users suffering from hemorrhoids or other skin ailments.

I. Compositions

In an aspect, a liquid composition comprises witch hazel; glycerin; dehydrated xanthan gum; and water. Witch hazel is a plant whose extract is a natural anti-inflammatory that can reduce the swelling and irritation of hemorrhoids, eczema, skin ulcers, insect bites, varicose veins, acne, and minor injuries and wounds. Additionally, witch hazel extract has been observed to possess hemostatic properties, meaning minor bleeding can be stopped upon application of the witch hazel extract. Composition described herein comprise a therapeutically active amount of witch hazel sufficient to provide anti-inflammatory and/or hemostatic properties to a user upon application. In some embodiments, the compositions comprise approximately 10-50 wt. %, 10-45 wt. %, 10-40 wt. %, 10-35 wt. %, 10-30 wt. %, 10-25 wt. %, 10-20 wt. %, 10-15 wt. %, 15-50 wt. %, 20-50 wt. %, 25-50 wt. %, 30-50 wt. %, 35-50 wt. %, 40-50 wt. %, 45-50 wt. %, 10 wt. %, 15 wt. %, 20 wt. %, 25 wt. %, 30 wt. %, 35 wt. %, 40 wt. %, 45 wt. %, or 50 wt. % witch hazel. In some cases the witch hazel present in the composition complies with United States Pharmacopeia (USP) National Formulary (NF) standards.

In some embodiments, compositions described herein comprise glycerin. While not intending to be bound by theory, glycerin is believed to form a protective barrier layer over hemorrhoids that slows drying of the tissues, reduces itching sensations, decreases evaporation of witch hazel extract components, and increases permeability and absorption of the witch hazel extract present in the composition. Glycerin can be present in the composition in amounts of 10-45 wt. %, 10-40 wt. %, 10-35 wt. %, 10-30 wt. %, 10-25 wt. %, 10-20 wt. %, 10-15 wt. %, 15-45 wt. %, 20-45 wt. %, 25-45 wt. %, 30-45 wt. %, 35-45 wt. %, 40-45 wt. %, 10 wt. %, 15 wt. %, 20 wt. %, 25 wt. %, 30 wt. %, 35 wt. %, 40 wt. %, or 45 wt. %, glycerin.

In amounts of 10-45 wt. %, glycerin is believed to act as a pharmaceutically active agent to form the previously described protective barrier layer. However, in some cases, lower quantities of glycerin can be used in the composition substantially as a pharmaceutically inactive agent, i.e. as an excipient. In cases where glycerin is used substantially as an excipient, glycerin can be present in the composition in amounts of approximately 0.5-10 wt. %, 0.5-9 wt. %, 0.5-8 wt. %, 0.5-7 wt. %, 0.5-6 wt. %, 0.5-5 wt. %, 0.5-4 wt. %, 0.5-3 wt. %, 0.5-2 wt. %, 0.5-1 wt. %, 1-10 wt. %, 2-10 wt. %, 3-10 wt. %, 4-10 wt. %, 5-10 wt. %, 6-10 wt. %, 7-10 wt. %, 8-10 wt. %, 9-10 wt. %, 0.5 wt. %, 1 wt. %, 2 wt. %, 3 wt. %, 4 wt. %, 5 wt. %, 6 wt. %, 7 wt. %, 8 wt. %, 9 wt. %, or 10 wt. %.

Compositions described herein comprise a thickening agent. One of the disadvantages to current commercial spray formulations is that they do not readily cling to a user's skin without dripping and/or running after spray application. As demonstrated in more detail in the Examples and Figures herein, conventional thickening agents used in spray formulations, such as xanthan gum, carboxymethyl cellulose, corn starch, tapioca starch, Bentone gel IPMV (INCI: isopropyl mytistate, stearalkonium hectorite, and propylene carbonate) and polyethylene glycol (PEG), displayed poor physical properties in spray compositions comprising witch hazel. As discussed herein, these conventional thickening agents displayed undesirable dripping and running after spray application.

Surprisingly, dehydrated xanthan gum ("dehydroxanthan gum") was found to provide desirable physical properties in spray composition comprising witch hazel. Compositions described herein comprising dehydroxanthan gum and witch hazel were found to reduce or eliminate the undesirable dripping and/or running of the composition after spray application. While dehydroxanthan gum is used in styling and cosmetic products, the use of dehydroxanthan gum as a thickening agent for spray delivery of pharmaceutically active ingredients is not conventional. In some cases, the dehydroxanthan gum has a viscosity between 25,000-35,000 cps when in a 1% aqueous solution or between 45,000 to 55,000 cps when in a 2% solution, which is equivalent to or higher than its parent polymer, xanthan gum. In some embodiments, dehydroxanthan gum is present in compositions described herein in amounts of 0.05-3 wt. %, 0.05-2.8 wt. %, 0.05-2.6 wt. %, 0.05-2.4 wt. %, 0.05-2.2 wt. %, 0.05-2 wt. %, 0.05-1.8 wt. %, 0.05-1.6 wt. %, 0.05-1.4 wt. %, 0.05-1.2 wt. %, 0.05-1 wt. %, 0.05-0.8 wt. %, 0.05-0.6 wt. %, 0.05-0.4 wt. %, 0.05-0.4 wt. %, 0.05-0.2 wt. %, 0.05-0.1 wt. %, 0.08-3 wt. %, 0.1-3 wt. %, 0.2-3 wt. %, 0.3-3 wt. %, 0.3-3 wt. %, 0.4-3 wt. %, 0.5-3 wt. %, 0.6-3 wt. %, 0.7-3 wt. %, 0.8-3 wt. %, 0.9-3 wt. %, 1-3 wt. %, 1.1-3 wt. %, 1.2-3 wt. %, 1.3-3 wt. %, 1.4-3 wt. %, 1.5-3 wt. %, 1.6-3 wt. %, 1.7-3 wt. %, 1.8-3 wt. %, 1.9-3 wt. %, 2-3 wt. %, 2.5-3 wt. %, 0.1-1 wt. %, 0.1-0.9 wt. %, 0.1-0.8 wt. %, 0.1-0.7 wt. %, 0.1-0.6 wt. %, 0.1-0.5 wt. %, 0.1-0.4 wt. %, 0.1-0.3 wt. %, 0.1-0.2 wt. %, up to 0.1 wt. %, up to 0.2 wt. %, up to 0.3 wt. %, up to 0.4 wt. %, up to 0.5 wt. %, up to 0.6 wt. %, up to 0.7 wt. %, up to 0.8 wt. %, up to 0.9 wt. %, up to 1 wt. %, up to 1.2 wt. %, up to 1.4 wt. %, up to 1.6 wt. %, up to 1.8 wt. %, up to 2 wt. %, up to 2.2 wt. %, up to 2.4 wt. %, up to 2.6 wt. %, up to 2.8 wt. %, or up to 3 wt. %. In a preferred embodiment, high molecular weight dehydroxanthan gum is used. However, in other embodiments, any molecular weight dehydroxanthan gum not inconsistent with the goals of this disclosure can be used.

In some embodiments, compositions described herein can further comprise one or more excipients. These excipients can include a chelating agent, an emollient, a humectant, a preservative, a pH modifier, a propellant or any combinations thereof.

Any chelating agent in any quantity not inconsistent with the objectives of this disclosure can be used. Exemplary chelating agents include disodium ethylenediaminetetraacetic acid (EDTA), edetic acid, or a combination of both. When present in the composition, chelating agents can be present in amounts of 0.05-0.3 wt. %, 0.05-0.28 wt. %, 0.05-0.25 wt. %, 0.05-0.2 wt. %, 0.05-0.18 wt. %, 0.05-0.15 wt. %, 0.05-0.12 wt. %, 0.05-0.1 wt. %, 0.05-0.08 wt. %, 0.08-0.3 wt. %, 0.1-0.3 wt. %, 0.12-0.3 wt. %, 0.15-0.3 wt. %, 0.18-0.3 wt. %, 0.2-0.3 wt. %, 0.22-0.3 wt. %, 0.25-0.3 wt. %, 0.28-0.3 wt. %, up to 0.05 wt. %, up to 0.07 wt. %, up to 0.1 wt. %, 0.05 wt. %, 0.07 wt. %, 0.1 wt. %, 0.12 wt. %, 0.15 wt. %, 0.18 wt. %, 0.2 wt. %, 0.22 wt. %, 0.25 wt. %, 0.28 wt. %, or 0.3 wt. %.

Emollients described herein can be any emollient in any quantity not inconsistent with the objectives of this disclosure. Typical emollients act as moisturizers to treat, prevent or alleviate rough, dry, or itchy skin and minor skin irritations. Exemplary emollients comprise *Aloe barbadensis* leaf juice, shea butter, vitamin E and vitamin E pharmaceutically acceptable salts, or any combination thereof. Emollients can be present in the composition in quantities sufficient to provide a moisturizing effect on the skin of a user. For example, an emollient can be present in the composition in amounts up to 0.5 wt. %, up to 0.8 wt. %, up to 1 wt. %, up to 1.2 wt. %, up to 1.5 wt. %, up to 1.8 wt. %, up to 2 wt. %, or up to 3 wt. %.

In some embodiments, humectants are present in the composition to reduce the loss of moisture from the skin of a user. Any humectant not inconsistent with the objectives of this disclosure can be used, including propylene glycol, sorbitol, glycerin, or any combination thereof. The humectant can be present in the composition in amounts up to 9 wt. %, up to 8 wt. %, up to 7 wt. %, up to 6 wt. %, up to 5 wt. %, up to 4 wt. %, up to 3 wt. %, up to 2 wt. %, up to 1 wt. %, up to 0.5 wt. %, or up to 0.2 wt. %. As can be appreciated by the skilled artisan, the humectant can be present in higher amounts, such as glycerin previously described herein, with the amount of humectant being dependent on its physical properties and potency.

In some instances, a preservative is present in the composition. The preservative can be any preservative not inconsistent with the objectives of this disclosure. Exemplary preservatives include sodium benzoate, benzyl alcohol, methyl paraben, propyl paraben, or any combination thereof. The preservative can be present in the composition in amounts up to 2 wt. %, up to 1.8 wt. %, up to 1.6 wt. %, up to 1.4 wt. %, up to 1.2 wt. %, up to 1 wt. %, up to 0.8 wt. %, up to 0.6 wt. %, up to 0.4 wt. %, up to 0.2 wt. %, or up to 0.1 wt. %.

In some embodiments, a pH modifier is present in the composition. Exemplary pH modifiers include sodium citrate, citric acid, acetic acid, maleic acid, tartaric acid, sodium acetate, sodium hydroxide, or any combination thereof, although any pH modifier not inconsistent with the objectives of this disclosure can be used. The quantity of pH modifiers present in the composition is dependent on the physical properties of the pH modifier (e.g. pKa), the desired final pH, at the like. In cases where sodium citrate and/or citric acid are used, sodium citrate can be present in an amount of 0.1-0.375 wt. % and citric acid at 0.25-0.05 wt. %.

Compositions described herein can further comprise water. Water can be present as the balance remaining in the wt. % of the composition. For example, water can be present in amounts ranging from 30-80 wt. %, 35-80 wt. %, 40-80 wt. %, 45-80 wt. %, 50-80 wt. %, 55-80 wt. %, 60-80 wt. %, 65-80 wt. %, 70-80 wt. %, 30-75 wt. %, 35-70 wt. %, 30-65 wt. %, 30-60 wt. %, 30-55 wt. %, 30-50 wt. %, 30-45 wt. %, 30-40 wt. %, 30-35 wt. %, 35-65 wt. %, 40-60 wt. %, 45-55 wt. %, 30 wt. %, 35 wt. %, 40 wt. %, 45 wt. %, 50 wt. %, 55 wt. %, 60 wt. %, 65 wt. %, 70 wt. %, 75 wt. %, or 80 wt. %.

In cases where compositions described herein are to be applied as spray formulations, the composition can comprise a propellant. Any propellant that is not inconsistent with the objectives of this disclosure can be used. For example, in some instances, a propellant can include isobutane, propane, N-butane, or any combination thereof.

In some embodiments, compositions described herein can further include additional active pharmaceutical ingredients, such as lidocaine, camphor, menthol, glycerin, other known topical numbing or cooling agents, or combinations thereof. Such additional active pharmaceutical ingredients, when present, can be used in combination with witch hazel, or in some instances, be used in place of witch hazel. The quantity of the additional active pharmaceutical ingredient present in the composition is specific to the physical properties of that ingredient. Thus, when present, the amount of additional active pharmaceutical ingredient can be any therapeutically effective amount not inconsistent with the objectives of this disclosure.

II. Methods

In another aspect, compositions described in Section I herein can be prepared by combining witch hazel; glycerin; and dehydrated xanthan gum in water. In some embodiments, compositions can be prepared by combining witch hazel; glycerin; and dehydrated xanthan gum in water, and additionally combining in the water a chelating agent, an emollient, a humectant, a preservative, a pH modifier, a propellant, or any combinations thereof described in Section I herein.

III. Methods of Treatment

In yet another aspect, a method of treating pain or inflammation in a mammalian subject comprising topically administering a therapeutically effective amount of any composition described in Section I herein to a mammalian subject in need thereof.

In some embodiments, a method of treating pain or inflammation exhibited by hemorrhoids, eczema, skin ulcers, insect bites, varicose veins, acne, and minor injuries and wounds comprises topically administering a therapeutically effective amount of any composition described in Section I herein to a mammalian subject in need thereof.

In some cases, a method of reducing swelling and irritation of hemorrhoids, eczema, skin ulcers, insect bites, varicose veins, acne, and minor injuries and wounds comprises topically administering a therapeutically effective amount of any composition described in Section I herein to a mammalian subject in need thereof.

In some cases, a mammalian subject is a human subject. In other cases, a mammalian subject is an animal subject.

Some embodiments described herein are further illustrated in the following non-limiting examples.

Example 1

Witch Hazel and Witch Hazel+Glycerin Prototypes

Two formulations were initially prepared to assess the physical properties of witch hazel, as shown in Table 1.

TABLE 1

Formulations 1 and 2

| Formulation No. | Composition |
|---|---|
| 1 | 20 wt. % Witch Hazel |
|   | 80 wt. % Water |
| 2 | 20 wt. % Witch Hazel |
|   | 15 wt. % Glycerin |
|   | 65 wt. % Water |

Formulation 1 was prepared by combining a witch hazel USP extract (in 14% alcohol) with water to give a 20 wt. % witch hazel solution. Formulation 2 was prepared by combining a witch hazel USP extract (in 14% alcohol) and glycerin with water to give a 20 wt. % witch hazel, 15 wt. % glycerin, and 65 wt. % water solution.

Both Formulations 1 and 2 were tested for viscosity properties and user "feel". FIG. 1 is a photographic image of each of the sprayed formulations, with the formulations being as follows: Formulation 1 (1a,1b) and Formulation 2 (2a,2b), where the "a" designation is for a 1 second spray time and the "b" designation is a 3 second spray time. For the viscosity testing, the 1 second and 3 second spray durations were conducted at a distance of 3 inches from a vertical cardboard surface using an isobutane propellant and a Moritz DU4833-19 actuator. As shown in FIG. 1, both Formulations 1 and 2 were observed to have a viscosity similar to water and to drip and run down the entire length of the vertical cardboard surface immediately upon spray application. It is noted that Formulation 1a in FIG. 1 is somewhat difficult to visually resolve. This composition ran down the entire vertical length of the surface (as also observed for Formulation 1b) and rapidly evaporated. Given that both formulations were runny, a suitable thickening agent was needed to achieve a formulation that readily clings to skin without dripping and running.

With respect to user "feel," Formulations 1 and 2 were applied to the skin of a test user using a 1 second spray burst at a distance of 3 inches. It was determined that the presence of glycerin in Formulation 2 provided a desirable protectant feel to a user, whereas Formulation 1 felt like water, with no desirable protectant feel.

Example 2

Conventional Thickening Agents

Given the undesirable physical properties observed for Formulations 1 and 2 in Example 1, various conventional thickening agents were combined with the composition of Formulation 2 in an attempt to achieve a formulation that readily clings to skin without dripping and running. These conventional thickening agents included xanthan gum, carboxymethyl cellulose (CMC), corn starch, tapioca starch, and bentone GEL IPM V (INCI name: Isopropyl myristate, stearalkonium hectorite, and propylene carbonate—sourced from Elementis). Formulations 3-10 were prepared by adding the corresponding thickening agent to Formulation 2 (20 wt. % witch hazel, 15 wt. % glycerin, with balance to 100% being water) in the amounts recited in Table 2. Formulation 11 was a unique variation that was composed of 40 wt. % Witch Hazel, 15 wt. % Glycerin, 3.99 wt. % PEG-400, and 0.5 wt. % Xanthan Gum, as shown in Table 3.

TABLE 2

Formulation 2 Combined with Conventional Thickening Agents

| Formulation No. | Thickening Agent |
|---|---|
| 3 | 0.3 wt. % Xanthan Gum |
| 4 | 0.5 wt. % CMC |
| 5 | 2 wt. % Corn Starch |
| 6 | 2 wt. % Tapioca Starch |
| 7 | 2 wt. % Bentone Gel |
| 8 | 2 wt. % Corn Starch, 0.5% Bentone Gel |
| 9 | 2 wt. % Tapioca Starch, 0.5% Bentone Gel |
| 10 | 0.5 wt. % Bentone Gel |

TABLE 3

Variation of Formulation 2 with Xanthan Gum

| Formulation No. | Thickening Agent |
|---|---|
| 11 | 40 wt. % Witch Hazel |
|    | 15 wt. % Glycerin |
|    | 3.99 wt. % PEG-400 |
|    | 0.5 wt. % Xanthan Gum |

Formulations 3-11 were each sprayed twice on a surface of vertically placed cardboard and the running and dripping properties of each formulation was compared. The propellant used to spray each formulation was isobutane and the spray actuator was a Moritz DU4833-19 or a VX/XL-200 Misty Button actuator. The type of actuator did not affect the spray properties of the formulations, with the spray being approximately equivalent between the two different actuators. The same volume of each formulation was sprayed on the surface from a distance of 3 inches by depressing an actuator on a pressurized container for 1 and 3 seconds, applying substantially the same volume of the formulation to the surface. User testing indicated that the average user applies a formulation for approximately 1 second on a given area, with a 3 second application being the highest spray duration observed during the testing. Generally, the 3 second spray time deposited an excessive amount of formulation on the given area but was used to observe the physical properties of the formulation on a surface when the formulation is present in very high amounts.

Figure 2:
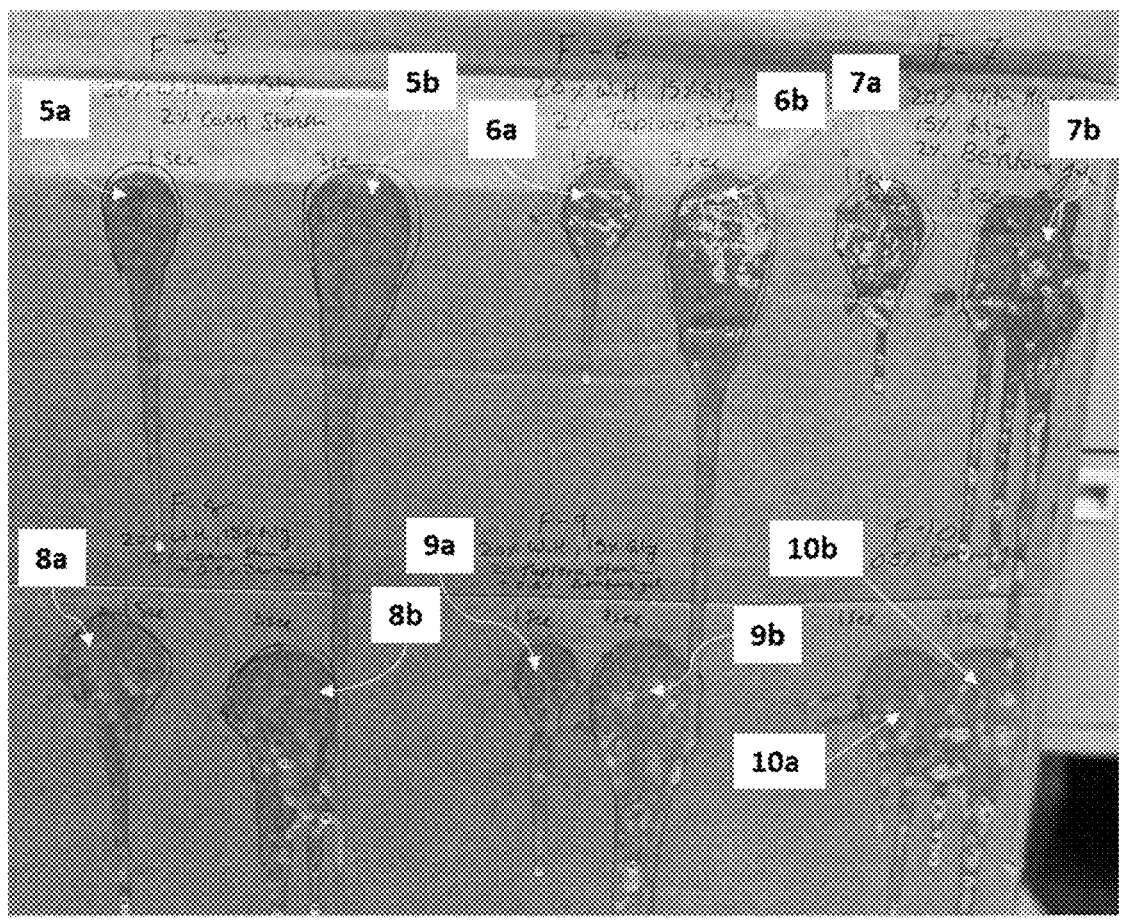
FIG. 2 is a photographic image comparing the physical properties of Formulations 5-10 described herein.
Figure 3:
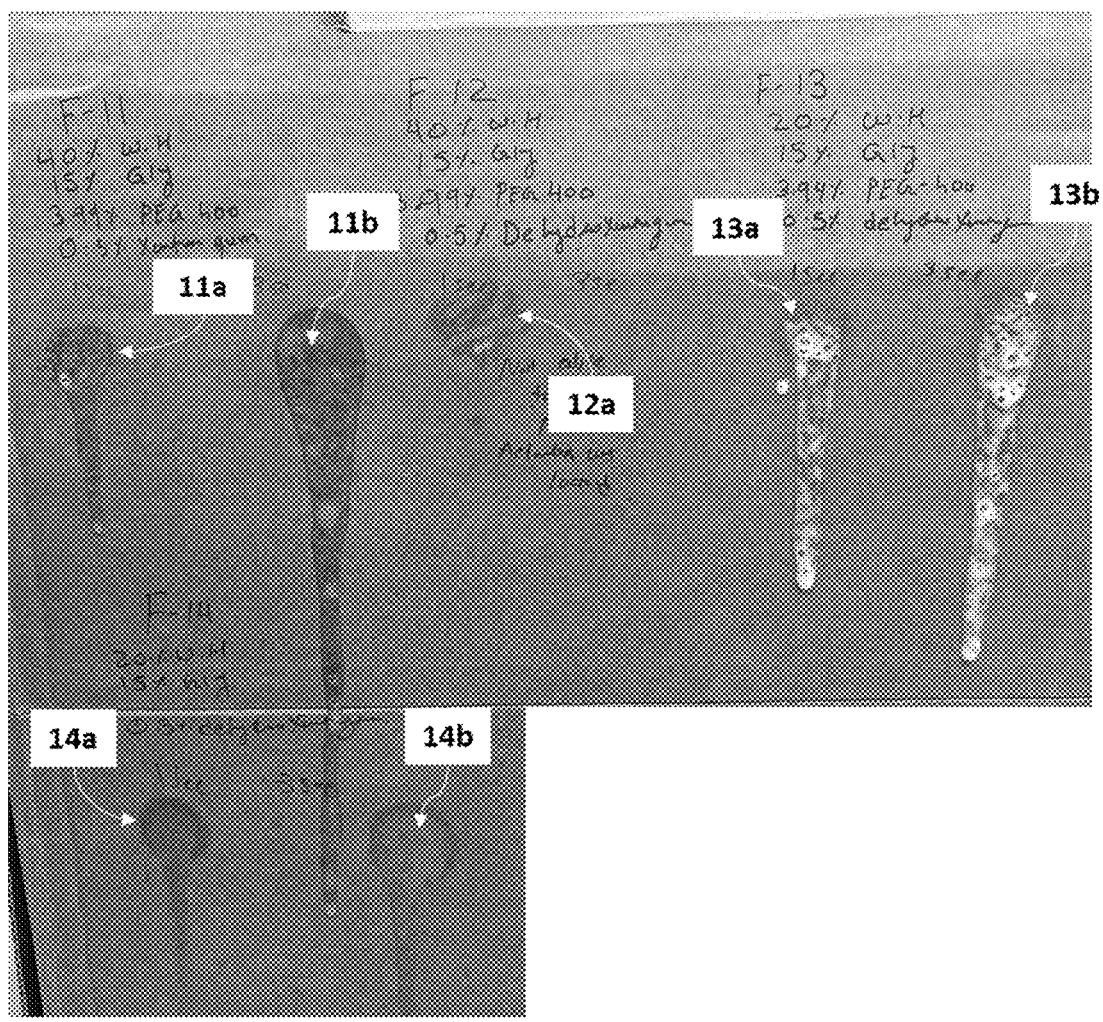
FIG. 3 is a photographic image comparing the physical properties of Formulations 11-14 described herein.

FIGS. 1-3 are photographic images of each of the sprayed formulations, with the formulations being as follows: Formulation 3 (3a,3b), Formulation 4 (4a,4b), Formulation 5 (5a,5b), Formulation 6 (6a,6b), Formulation 7 (7a,7b), Formulation 8 (8a,8b), Formulation 9 (9a,9b), Formulation 10 (10a,10b), and Formulation 11 (11a,11b), where the "a" designation is for the 1 second spray time and the "b" designation is the 3 second spray time. Formulation 1 (1a,1b) and Formulation 2 (2a,2b) were used as controls As shown in FIGS. 1-3, each of Formulations 3-11 displayed undesirable physical properties after spray application on a surface, with all formulations exhibiting running and dripping after the 1 and 3 second spray applications. As expected, Formulations 1 and 2 controls showed extensive dripping and running immediately upon application.

The poorest performing formulation was Formulation 4 having 0.5 wt. % CMC. Formulation 4 dripped and ran rapidly and immediately upon dispensing for both the 1 and 3 second application times, as shown in FIG. 1. This result is surprising, because CMC is a common thickening agent that was expected to exhibit desirable physical properties.

Formulation 3, having 0.3 wt. % xanthan gum, displayed improved physical properties, exhibiting reduced dripping and slower running compared to the controls and to Formulation 4 for the 1 second application time. However, as seen in FIG. 1, Formulation 3 did display excessive and undesirable dripping and running for the 3 second application time, albeit at a slower rate and length than the controls and Formulation 4. Like the CMC results, these results are surprising, because xanthan gum is also a common thickening agent that was expected to exhibit desirable physical properties.

Formulations 5-10 which contained one or more common thickening agents each displayed physical properties that fell between those of xanthan gum and CMC in Formulations 3 and 4, respectively, as shown in FIG. 2. Formulations 5 (2 wt. % corn starch) and 6 (2 wt. % tapioca starch) were observed to exhibit similar physical properties, with both displaying excessive dripping and running properties. The use of 2 wt. % bentone gel in Formulation 7 did show improvements over Formulations 4 and 5, with less running being observed. However, while Formulation 5 had better "cling" to the surface, the formulation left a sticky/tacky after-feel and generated an excessive amount of foaming when sprayed. Decreasing the amount of bentone gel to 0.5 wt. % (Formulation 10) resulted in a composition that still exhibited the desired surface "cling," but the formulation still exhibited undesirable running and dripping. Additionally, even at lower concentrations the bentone gel caused excessive foaming when sprayed. While not intending to be bound by theory, it is believed that because bentone gel is hydrophobic (oil-based), solubilization in the hydrophilic aqueous media is likely the cause of the foaming.

Formulations 8 and 9 were mixtures of corn starch/bentone gel and tapioca starch/bentone gel, respectively. Again, the presence of bentone gel in the formulations caused excessive foaming when sprayed, and the presence of a starch did not alleviate this problem. Moreover, both Formulations 8 and 9 displayed undesirable dripping and running properties. In summary, none of Formulations 3-10 exhibited the desirable properties of being dripless and runless at either the 1 second or 3 second application times using conventional thickening agents.

Of the different conventional thickening agents, Formulation 3 with xanthan gum exhibited the least amount of dripping and running after spray application. However, as discussed, the level of dripping and running was still unacceptable. Formulation 11 was prepared to test whether the combination of xanthan gum and PEG-400 would improve the physical properties of the formulation. As shown in FIG. 3, the increased concentration of xanthan gum to 0.5 wt. % and the addition of PEG-400 did not result in improved physical properties over Formulation 3. Instead, Formulation 11 was observed to drip and run similarly to those observed for Formulation 3. Additionally, the presence of PEG-400 in the formulation dramatically increased the drying time of the formulation, rendering Formulation 11 unsuitable.

In summary, none of the conventional thickening agents described in Formulations 3-11 reduced dripping and running when the formulations were sprayed on a vertical surface.

Example 3

Dehydroxanthan Gum as a Thickening Agent

With the conventional thickening agents (described in Example 2) failing to modify the viscosity of Formulation 2 and prevent dripping and running, non-conventional thickening agents were explored. Unexpectedly, it was discovered that dehydrated xanthan gum (dehydroxanthan gum) outperformed all the conventional thickening agents previous explored in Example 2, including xanthan gum. As detailed herein, dehydroxanthan gum provided better "cling to surface" properties, with little to no dripping and running after spray application.

Formulations 12-14 were prepared to explore the physical properties of dehydroxanthan gum, either as the sole thickening agent (e.g. Formulation 14) or in combination with PEG-400 at different concentrations of witch hazel (e.g. Formulations 12 and 13). Table 4 describes the compositions of Formulation 12-14, which were prepared combining a witch hazel USP extract (in 14% alcohol) with the remaining compositional ingredients in the listed ratios. Each formulation was then tested in the same manner as described for Formulations 1-11 described in Examples 1 and 2 herein using the same nomenclature denoting a 1 second spray time and a 3 second spray time (e.g. Formulation 11 (11a, 11b)).

TABLE 4

New Formulation Variations

| Formulation No. | Composition |
| --- | --- |
| 12 | 40 wt. % Witch Hazel |
|  | 15 wt. % Glycerin |
|  | 3.99 wt. % PEG-400 |
|  | 0.5 wt. % Dehydroxanthan Gum |
|  | 40.51 wt. % Water |
| 13 | 20 wt. % Witch Hazel |
|  | 15 wt. % Glycerin |
|  | 3.99 wt. % w PEG-400 |
|  | 0.5 wt. % Dehydroxanthan Gum |
|  | 60.51 wt. % Water |
| 14 | 20 wt. % Witch Hazel |
|  | 15 wt. % Glycerin |
|  | 0.3 wt. % Dehydroxanthan Gum |
|  | 64.7 wt. % Water |

Formulation 14 was prepared by adding 0.3 wt. % dehydroxanthan gum (Amaze XT) into Formulation 2 and spraying the formulation on the same surface as the formulations described in Example 2. As shown in FIG. 3, when applied to the vertical surface, Formulation 14 (10) remained stationary with little to no running or dripping, in contrast to the other formulations, which displayed extensive running and dripping. While Formulation 14 did exhibit some running, the volume of liquid forming the runs was much lower than the volume observed for other formulations. Instead, the majority of sprayed Formulation 14 remained stationary on the surface. This is unexpected, especially given that 0.3 wt. % of xanthan gum (Formulation 3) exhibited rapid dripping and running at the equivalent concentrations (see FIG. 2). It was expected that dehydroxanthan gum would display nearly identical physical properties as xanthan gum, which it did not.

Formulations 12 and 13 were prepared to test whether a combination of PEG-400 and dehydroxanthan gum would possess superior physical properties at difference concentrations of witch hazel. However, as shown in FIG. 3, Formulation 13 exhibited excessive foaming when sprayed, and extensive running and dripping was observed. Moreover, the presence of PEG in the formulation dramatically increased the drying time of the formulation, rendering Formulation 13 unusable. Thus, it is preferable to use compositions free of PEG. However, in some cases very low levels of PEG may provide suitable physical characteristics.

Formulation 12 was unable to be tested due to the spray applicator clogging. However, it was believed that the physical properties of Formulation 12 would be similar to Formulation 13.

Additional variations of Formulation 14 having greater than 0.3 wt. % of dehydroxanthan gum were prepared (results not shown in Figures), and it was discovered that for effectuating spray application, it is preferred that dehydroxanthan gum not be present in amounts greater than 3 wt. %, because generally such composition are too viscous for spray applications.

In summary, dehydroxanthan gum-containing formulations unexpectedly possessed superior physical properties than the conventional thickening agents described in Example 2. Additionally, it was observed that formulations with dehydroxanthan gum displayed reduced or eliminated dripping and running after spray application, whereas formulations with even closely related thickening agents (such as xanthan gum) unexpectedly did not reduce or eliminate dripping and running after spray application.

The invention claimed is:

1. A spray composition comprising:

a liquid comprising:

witch hazel;

glycerin;

0.05 to 3 wt. % dehydrated xanthan gum; and water, and a propellant.

2. The composition of claim 1, wherein the dehydrated xanthan gum is present in the composition in an amount of 0.05 to 1.0 wt. %.

3. The composition of claim 1, wherein the dehydrated xanthan gum is present in the composition in an amount of 0.05 to 0.5 wt. %.

4. The composition of claim 1 comprising 0.1-0.5 wt. % dehydrated xanthan gum.

5. The composition of claim 1 comprising 10-50 wt. % witch hazel.

6. The composition of claim 1 comprising 10-45 wt. % glycerin.

7. The composition of claim 1 comprising 30-70 wt. % water.

8. The composition of claim 1 further comprising a chelating agent, an emollient, a humectant, a preservative, a pH modifier, or any combination thereof.

9. The composition of claim 8, wherein the chelating agent comprises disodium ethylenediaminetetraacetic acid ("EDTA"), edetic acid, or a combination of both.

10. The composition of claim 8, wherein the emollient comprises one or more of *Aloe barbadensis* leaf juice, shea butter, vitamin E or pharmaceutically acceptable salts thereof, or any combination thereof.

11. The composition of claim 8, wherein the humectant comprises one or more of propylene glycol, sorbitol, glycerin, or any combination thereof.

12. The composition of claim 8, wherein the preservative comprises one or more of sodium benzoate, benzyl alcohol, methyl paraben, propyl paraben, or any combination thereof.

13. The composition of claim 8, wherein the pH modifier comprises one or more of sodium citrate, citric acid, acetic acid, maleic acid, tartaric acid, sodium acetate, sodium hydroxide, potassium hydroxide, or any combination thereof.

14. The composition of claim 1, wherein the propellant comprises one or more of isobutane, propane, N-butane, or any combination thereof.

15. A method of treating pain or inflammation in a mammalian subject comprising topically administering a therapeutically effective amount of the composition according to claim 1 to a mammalian subject in need thereof.

16. A spray composition comprising:

a liquid comprising:

10-50 wt. % witch hazel;

10-45 wt. % glycerin;

0.05 to 1 wt. % dehydrated xanthan gum; and water, and a propellant.

17. A method of treating pain or inflammation in a mammalian subject comprising topically administering a therapeutically effective amount of the composition according to claim 16 to a mammalian subject in need thereof.

* * * * *